United States Patent [19]

Havemeyer et al.

[11] 4,342,784

[45] Aug. 3, 1982

[54] CHEMICAL COMPOSITIONS AND METHOD OF UTILIZATION

[75] Inventors: Ruth N. Havemeyer, Palo Alto, Calif.; Gilman N. Cyr, Piscataway, N.J.

[73] Assignee: E. R. Squibb & Sons, Inc., Princeton, N.J.

[21] Appl. No.: 261,844

[22] Filed: Jun. 12, 1972

Related U.S. Application Data

[63] Continuation of Ser. No. 783,120, Dec. 11, 1968, abandoned, which is a continuation-in-part of Ser. No. 401,963, Oct. 6, 1964, abandoned.

[51] Int. Cl.$^3$ ............... A61K 31/10; A61K 31/60; A61K 31/58; A61K 31/74
[52] U.S. Cl. ............................... 424/337; 424/78; 424/81; 424/238; 424/240; 424/241; 424/230; 424/232; 424/358
[58] Field of Search ..................... 424/78, 337, 81

[56] References Cited

U.S. PATENT DOCUMENTS 3,011,950 12/1961 Mehaffey ................. 424/59 X
3,549,770 12/1970 Herschler et al. ............ 424/337

FOREIGN PATENT DOCUMENTS 644613 3/1964 Belgium .
644614 3/1964 Belgium .
644615 3/1964 Belgium .
65/5363 10/1965 South Africa .

OTHER PUBLICATIONS

Block Drug & Cosmetic Industry 95(3): 342, 345, 346, 462–465 (1964), "Dimethyl Sulfoxide–Medicinal and Pharmaceutical Aspects".
Secard (I) Drug & Cosmetic Industry 89(6): 718–720, 763, 804, 811, 822, Dec. 1961, Carbopol Cosmetics.
Secard (II) Drug & Cosmetic Industry 90(1): 28–30, 113, 115, 116, Jan. 1962, Carbopol Pharmaceuticals.
Marson Bolletino Chimico Farmaceutico 102: 109–124 (1963), "Dimethysulfoxide an Aquo–Mimetic Solvent", 36 pp., PTO translation.
Brown (I) Ind. Med. Surg. 35; 777–781, Sep. 1966.
Brown (II) Ann. N.Y. Acad. Sci. 141 (1): 496–505, Mar. 15, 1967.

Primary Examiner—Shep K. Rose
Attorney, Agent, or Firm—L. S. Levinson

[57] ABSTRACT

Disclosed herein is a pharmaceutically active gelled composition of dimethyl sulfoxide for utilization in the treatment of musculoskeletal disorders.

3 Claims, No Drawings

CHEMICAL COMPOSITIONS AND METHOD OF UTILIZATION

RELATED APPLICATION

This application is a continuation of my copending application, Ser. No. 783,120, filed Dec. 11, 1968, now abandoned, which application in turn is a continuation-in-part of my copending application Ser. No. 401,963, filed Oct. 6, 1964, now abandoned.

This invention relates to and has as its object the provision of new therapeutically useful compositions. More particularly, this invention relates to novel compositions containing as one of its principal ingredients dimethyl sulfoxide.

Dimethyl sulfoxide has been discovered to possess certain therapeutic properties which make the administration thereof very desirable. Although at room temperature, dimethyl sulfoxide is a liquid, in certain instances, efficient administration of the substance is not practical. For example, in some veterinary applications where the substance is applied to the animal by hand, the person applying the medicament is exposed to and absorbs as much as the animal being treated.

In addition, in some instances it has been found that the liquid preparations of dimethyl sulfoxide presently available are very rapidly absorbed and the therapeutic effect thereof is quickly dissipated.

It is an object of this invention to provide a therapeutic composition comprising dimethyl sulfoxide which composition may be efficiently and easily administered.

Another object of this invention is the provision of a long-acting therapeutic composition comprising dimethyl sulfoxide.

Other objects of this invention will become apparent from a further reading of the instant specification.

It has now been discovered that the disadvantages presently residing in the employment of therapeutic compositions comprising dimethyl sulfoxide may be overcome by the provision of a gelled dimethyl sulfoxide composition. This gelled composition may be prepared by combining a suitable amount of dimethyl sulfoxide with a suitable amount of the novel gelling agents of this invention.

Among the novel gelling agents which may be employed in the practice of this invention, there may be included inter alia, carboxy vinyl polymers (e.g., Carbopol 934, Carbopol 940; B. F. Goodrich Co.); cellulose ethers (e.g., hydroxy ethyl ethers of cellulose, sold under the trade name Natrosol 250 HR by Hercules Powder Co.); nonionic cellulose ethers (e.g., sold under the trade name Klucel HA by Hercules Powder Co.); methyl ether of cellulose (e.g., sold under the trade name Methocel by Dow Chemical Co.); polyvinyl alcohols (e.g., Elvanol, sold by DuPont Chemical Co.); and carrageen derivatives (e.g., sodium carrageenate, sold under the trade name Viscarin by Marine Colloids, Inc.).

The amount of the gelling agent satisfactorily employable in the practice of this invention has been found to vary from about 0.2% to about 20.0% by weight of the dimethyl sulfoxide. Most preferably, it has been found that satisfactory results are obtained when the amount of gelling agent employed is from about 1 to 2% by weight of the dimethyl sulfoxide.

The novel compositions of this invention may be prepared by thoroughly admixing the novel gelling agents of this invention with the dimethyl sulfoxide. In those embodiments where the gelling agent is a carboxy vinyl polymer, the admixture may then be neutralized as by treatment with a neutralizing agent, for example, triethanolamine, N-methylglucamine, sodium hydroxide, triethylamine, monoethanolamine, to yield the final compositions of this invention.

Absolute dimethyl sulfoxide may be employed in the practice of this invention or alternatively the dimethyl sulfoxide may be diluted as by the addition of water, ethanol, or other pharmaceutically acceptable solvent thereto. Thus, satisfactory results are obtained when dimethyl sulfoxide is present in the final composition of this invention in a concentration of from about 99.8 to about 10.0% by weight. Most preferably, satisfactory results are obtained when the final compositions of this invention comprise from 99.8 to about 90.0% by weight of dimethyl sulfoxide.

The gelled dimethyl sulfoxide composition of the invention has been found to be successful in the treatment of musculoskeletal disorders and trauma. Among the disorders successfully treated with the instant gelled formulation, are acute strains and sprains.

In addition to possessing therapeutic properties of its own, dimethyl sulfoxide is known to be a powerful translocation agent, in that it quickly penetrates membranes and in many instances carries with it any medicament dissolved therein. It has surprisingly been found that this phenomenon also occurs even when dimethyl sulfoxide is in the novel gelled composition of the instant invention. Thus, compositions comprising dimethyl sulfoxide (either absolute or diluted), the novel gelling agents of this invention and translocatable medicaments may be very satisfactorily employed in the treatment of many conditions not heretofore amenable to such therapy. The medicaments which may beneficially be included in the novel compositions of this invention include such medicaments as anti-inflammatory steroids, for example, triamcinolone acetonide; antimicrobial antifungal agents, for example, amphotericin B; antimicrobial antibiotic agents, for example, tetracycline; analgesics, for example, methyl salicylate; antibacterial agents, for example, chlorhydroxyquinolone; antifungal agents, for example, hydroxy pyridine derivatives; and other like agents.

The compositions of this invention which contain an active medicament other than dimethyl sulfoxide may by comprised of from about 99.8 to 10.0% by weight of dimethyl sulfoxide, from about 0.25 to about 2.0% by weight of the novel gelling agent and from about 0.01 to about 20% by weight of the medicament employed.

The invention may be further illustrated by the following examples.

EXAMPLE 1

1.0 Grams of carboxy vinyl polymer powder (Carbopol 940, B. F. Goodrich Co.) is sprinkled into 90 grams of rapidly stirred dimethyl sulfoxide. After the carboxy vinyl polymer powder has been added, the mixture is stirred until all the particles have been wetted and dissolved. 0.5 Grams of triethanolamine is dissolved into 10 grams of dimethyl sulfoxide and this solution is added to the carboxy vinyl polymer powder—dimethyl sulfoxide mixture with stirring to yield a dimethyl sulfoxide gel.

Similarly, like results are obtained if equivalent amounts of N-methylglucamine and monoethanolamine are substituted for triethylamine.

Following the procedure of Example 1, but substituting a mixture of 80 grams of dimethyl sulfoxide and 10 grams of water for the 90 grams of dimethyl sulfoxide, like results are obtained.

EXAMPLE 2

To 90 grams of dimethyl sulfoxide there is added 10 mg. of triamcinolone acetonide. 1 Gram of carboxy vinyl polymer powder (Carbopol 940, B. F. Goodrich Co.) is sprinkled into the rapidly stirred resultant dimethyl sulfoxide solution. After the carboxy vinyl polymer powder has been added, the mixture is stirred until all of the particles are wetted and dissolved, 0.5 Grams of triethylamine is then dissolved in 10 grams of water and the resultant solution is added to the carboxy vinyl polymer—dimethyl sulfoxide mixture with stirring to yield the desired gelled composition.

EXAMPLE 3

10 Grams of triamcinolone acetonide and 1 gram of chlorhydroxyquinolone are dissolved in 90 grams of dimethyl sulfoxide. 2.0 Grams of carboxy vinyl polymer powder (Carbopol 940, B. F. Goodrich Co.) is sprinkled into the rapidly stirred dimethyl sulfoxide solution until all of the particles have been wetted and dissolved. 1 Gram of triethanolamine is then dissolved in 10 grams of dimethyl sulfoxide and the resultant solution is added to the carboxy vinyl polymer—dimethyl sulfoxide mixture with stirring to yield the desired gelled composition.

EXAMPLE 4

10 Grams of dimethyl sulfoxide and 80 grams of water are mixed, and 1 gram of carboxy vinyl polymer powder (Carbopol 940, B. F. Goodrich Co.) is sprinkled into the rapidly stirred solution. This mixture is stirred until all of the particles have been wetted and dissolved. 0.5 Grams of triethanolamine is dissolved in 10 grams of water, and the resultant solution is added to the carboxy vinyl polymer—dimethyl sulfoxide mixture with stirring to yield the desired gelled composition.

EXAMPLE 5

Similarly, following the procedures set forth in Examples 1 through 4, without employing a neutralizing agent, but substituting for the carboxy vinyl polymer powder equivalent amounts of the following gelling agents, like results are obtained: hydroxy ethyl ethers of cellulose (e.g., Natrosol, 250 HR by Hercules Powder Co.); nonionic cellulose ethers (e.g., Klucel HA by Hercules Powder Co.); methyl ether of cellulose (e.g., Methocel by Dow Chemical Co.); polyvinyl alcohols (e.g., Elvanol, by DuPont Chemical Co.); sodium carrageenate (e.g., Viscarin, by Marine Colloids, Inc.).

EXAMPLE 6

Similarly, following the procedure set forth in Examples 2 and 3, but substituting equivalent amounts of such medicaments as amphotericin B, tetracycline, methyl salicylate and hydroxy pyridinethione, there is obtained gelled compositions of therapeutic value.

The advantage of gelled formulations of 70% solution and over essentially reside in the feature that by topical application of the gel there was no skin pooling of DMSO as occurred when the solution was applied.

This provided for a greater uniformity of application and allowed the patient to be mobile whereas when solutions were applied, it was necessary to immobilize the patient to obviate the effect of gravity on the applied medication.

The invention may be variously otherwise embodied within the scope of the appended claims.

What is claimed is:

1. A method of administering liquid dimethylsulfoxide cutaneously and topically to humans and animals in amounts effective for therapeutic action without having the dimethylsulfoxide run off the skin and without causing significant irritation of the skin, said method comprising
    (a) applying to the surface of the skin at and surrounding the site of the disorder being treated an ionicly sensitive, semi-solid gel consisting essentially of
        (i) a mixture of dimethylsulfoxide and water wherein the dimethylsulfoxide is present in a concentration of about 99.8% to about 10% by weight in the gel composition,
        (ii) carboxy polymethylene water-soluble resin in an amount from about 0.2% to about 20.0% by weight of the gel composition and,
        (iii) a neutralizing agent selected from the group consisting of triethanolamine, N-methylglucamine, sodium hydroxide, triethylamine, or monoethanolamine; and
    (b) maintaining said semi-solid gel in contact with said skin for a period sufficient to enable the salt normally present at the surface of the skin to gradually break the semi-solid gel composition and thereby slowly release the liquid mixture of dimethylsulfoxide and water over the surface of the skin where the semi-solid gel was applied.

2. The method of claim 1, wherein the dimethylsulfoxide is present in a concentration of about 99.8% to about 90% by weight in the gel composition.

3. The method of claim 2, wherein the carboxy polymethylene water-soluble resin is present in an amount from about 1% to about 2% by weight of the dimethylsulfoxide.

* * * * *